US00PP33985P2

(12) United States Plant Patent
Hansen

(10) Patent No.: US PP33,985 P2
(45) Date of Patent: Mar. 1, 2022

(54) **X *MANGAVE* PLANT NAMED 'DRAGON LADY'**

(50) Latin Name: **x *Mangave* hybrid**
Varietal Denomination: Dragon Lady

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,490

(22) Filed: Jul. 16, 2021

(51) Int. Cl.
*A01H 5/12* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 5/12
See application file for complete search history.

*Primary Examiner* — Kent L Bell

(57) ABSTRACT

A new and unique x *Mangave* plant named 'Dragon Lady' characterized by a compact, rounded mound of fleshy, linear to lanceolate, leaves that are wavy, twisted, slightly-arching and terminate in a flexible apical spine. The leaves have numerous small, flexible marginal teeth pointing outwardly. Foliage is variegated with the leaf centers becoming creamy-yellow with cherry-red spots. The new plant is suitable for the garden or as a potted plant in the garden or home.

1 Drawing Sheet

Botanical classification: x *Mangave* hybrid.
Variety denomination: 'Dragon Lady'.

BACKGROUND OF THE INVENTION

The present invention relates to the new and distinct x *Mangave* hybrid plant, x *Mangave* 'Dragon Lady' that was discovered by the inventor at a wholesale perennial nursery in Zeeland, Mich., USA as whole plant mutation of x *Mangave* 'Desert Dragon' U.S. Plant Pat. No. 31,311. The new mutation was discovered on Feb. 6, 2018. Through trials at the same nursery the plant was assigned the code number 18-SP-MANG-637-B. The new plant has been successfully asexually propagated by basal offsets at the same nursery in Zeeland, Mich. originally in 2021. The asexual propagation has been found to produce stable and identical plants that maintain all the unique characteristics of the original plant in multiple generations.

BRIEF SUMMARY OF THE INVENTION x *Mangave* 'Dragon Lady' differs from its parent as well as all other *Manfreda, Agave* and x *Mangave* known to the applicant. The sport parent, 'Desert Dragon', does not have the variegated foliage with the creamy-yellow center with clear purplish-red spotting.

The nearest comparison plants are: 'Carnival' U.S. Plant Pat. No. 31,249, 'Bridal Falls' U.S. Plant Pat. No. 33,080, 'Foxy Lady' U.S. Plant Pat. No. 33,032, 'Life on Mars' U.S. Plant Pat. No. 32,939, 'Pineapple Punch' U.S. Plant Pat. No. 32,041, and 'Center of Attention' U.S. Plant Pat. No. 33,630.

'Carnival' has a longer, flatter leaf with a yellow center and without the sinuate channeled form. 'Bridal Falls' has a larger habit or arching foliage and the leaves have a white margin and there are few if any purplish spots. 'Life on Mars' is a much larger plant with longer and broader leaves that have a yellowish margin and darker center variegation, with purplish-red spots nearly connecting. 'Pineapple Punch' has more upright habit and longer and flatter foliage with the variegation on the margin producing a yellowish band with cherry-red spots and the center is greyed-green with speckled burgundy. 'Foxy Lady' has broader and more arching and glaucous foliage with a creamy margin and much larger marginal teeth. 'Center of Attention' has flatter leaves that are greyish-purple with a lighter center of moderate purplish-red.

'Dragon Lady' is unique from all of the above cultivars and all *Agave*, x *Mangave* and *Manfreda* known to the inventor by the following combined traits:

1. Compact, rounded mound of linear to lanceolate, deeply channeled, wavy, twisted, slightly arching, sarcous leaves;
2. Leaf margins develop large, dense, dark greyed-purple spotting on a glaucous, light greyed-purple background;
3. Leaf centers are variegated with creamy-yellow and cherry-red spots;
4. Leaf margins have many, small, flexible, marginal teeth;
5. Moderate growth rate;

BRIEF DESCRIPTION OF THE DRAWING

The photograph of x *Mangave* 'Dragon Lady' demonstrates the overall appearance of the new plant including the unique traits as a two-year-old plant grown in a greenhouse and moved to a full-sun trial garden in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
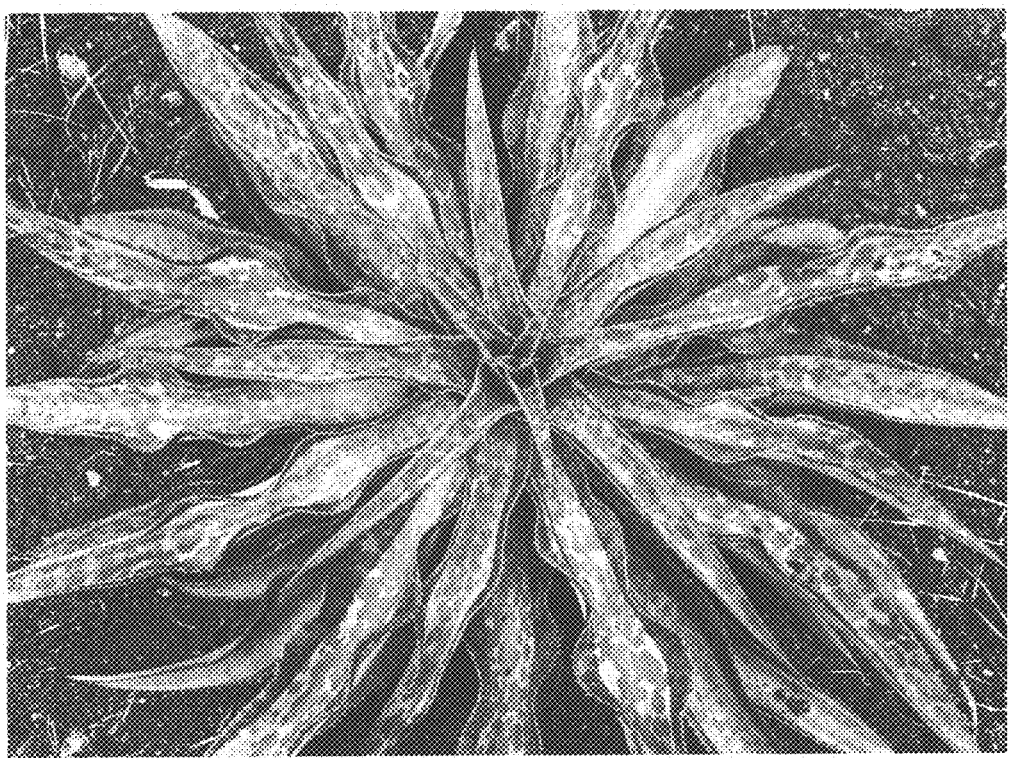
FIG. 1 shows a plant from above.
Figure 2:
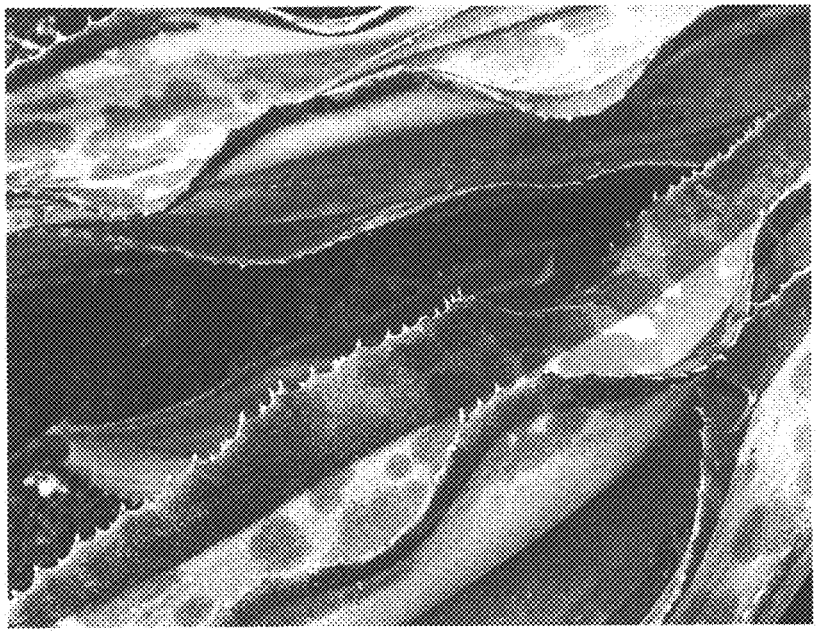
FIG. 2 shows a close-up of the variegation coloration and marginal teeth.

The following descriptions and color references are based on the 2015 edition of The Royal Horticultural Society Colour Chart except where common dictionary terms are used. The new plant, x *Mangave* 'Dragon Lady', has not been observed under all possible environments. The phenotype may vary slightly with different environmental conditions, such as temperature, light, fertility, moisture and maturity levels, but without any change in the genotype. The following observations and size descriptions are of a two-year-old plant in a trial garden in Zeeland, Mich. with supplemental water and fertilizer as needed.

Parentage: Whole plant mutation of 'Desert Dragon';

Propagation: By basal offshoot division;

Time to initiate roots: About 21 days;

Growth rate: Moderate;

Crop time: About 16 to 22 weeks to finish in a 3.8 liter container from a 35 mm tissue culture growing at about 21° C.;

Rooting habit: Fleshy, lightly branching, with roots up to 25 cm long;

Root color: Nearest RHS 158B;

Plant shape and habit: Succulent herbaceous perennial with basal rosettes of about 46 leaves radially emerging outwardly flow central stem, producing a radially-symmetrical, rounded mound with maturity;

Plant size: Foliage height about 10.0 cm tall from soil line to the top of the leaves and about 39.0 cm wide at the widest point just above soil level;

Stem: To about 2.5 cm across and about 2.2 cm long; covered with foliage, not visible;

Foliage description: Linear to lanceolate; simple; sessile; bi-laterally symmetrical; sarcous; apex narrowly acute with flexible terminal spine; base truncate; older lower leaves slightly concavo-convex and younger upper leaves flat; margins undulate, serrate with small, flexible, outwardly pointing teeth; both adaxial and abaxial glabrous and glaucous;

Apical spine: About 6.0 mm long and 1.0 mmm wide;

Marginal teeth: Small, flexible even when mature; protruding about 1.0 mm long from margin and 1.0 mm wide at base, average spacing about 1.5 mm apart;

Leaf size: To about 19.0 cm long, about 30.0 mm wide toward middle; center base about 6.0 mm thick at basal midrib; older leaves channeled to about 15.0 mm deep; average about 16.0 cm long, 28.0 mm wide and 5.0 mm thick in longitudinal center; spots on both adaxial and abaxial vary from 1.0 mm to 9.0 mm across and frequently overlap;

Variegation width: Margins to about 10.0 mm wide on adaxial side and 6.0 mm wide on abaxial side; with rare and irregular margin portions parallel and jetting into margin on adaxial side;

Foliage fragrance: None observed;

Leaf number: About 46 per plant;

Leaf blade color:

*Adaxial* (*low light*).—Young and mature leaf margins between RHS NN137A and RHS 136A with spots nearest RHS 139A.

*Abaxial* (*low light*).—Young and mature leaf margins nearest RHS N138B with spots of nearest NN137A.

*Adaxial* (*low light*).—Young and mature leaf centers between RHS 145D and RHS N144D with spots nearest. RHS 147B.

*Abaxial* (*low light*).—Young and mature leaf centers between RHS 160D and RHS 145C with spots nearest RHS 146D.

*Adaxial* (*high light*).—Young leaf margins blend between RHS 139A and RHS N138A with spots between RHS N187A and RHS N187B; mature leaf margins blend between RHS NN137A and RHS 139A with spots nearest RHS N187A, with a light blush of greyed-purple between RHS N187C and RHS N187D.

*Abaxial* (*high light*).—Young leaf margins blend nearest RHS 137A and RHS NN137D with spots between RHS N187B and RHS N187C; mature leaf margins nearest RHS NN137A with spots nearest RHS N187A.

*Adaxial* (*high light*).—Young leaf centers nearest RHS N148C with spots between RHS N187A and RHS N187B; mature leaf centers variable between RHS 18A and blend between RHS 160D and RHS 161D with spotting nearest RHS 185C.

*Abaxial* (*high light*).—Young leaf centers blend between RHS 195C and RHS 147D with spots between RHS 185C and RHS 185D; mature leaf centers blend between RHS 158D and RHS 160D with spots between RHS 185B and RHS 185C.

*Teeth.*—Nearest RHS 155B with moderate blush nearest RHS 186B.

*Apical spine.*—Nearest RHS N200B.

Petiole: Leaves sessile;

Veins: Parallel; not distinct abaxial or adaxial;

Flower description: Not yet observed;

Fruit and seed: Not yet observed;

Disease resistance: x *Mangave* 'Dragon Lady' has not been observed to be resistant or susceptible to diseases beyond that which is normal for x *Mangave, Agave* or *Manfreda.*

Growing conditions: The new plant is xeromorphic and survives well with minimal water once established.

Winter hardiness: The new plant is estimated to be hardy at least from USDA zone 9. Full extent of winter hardiness has not been tested.

It is claimed:

1. A new and distinct cultivar of ornamental x *Mangave* plant named 'Dragon Lady' as herein described and illustrated.

* * * * *